United States Patent [19]

Moore

[11] 4,172,082

[45] Oct. 23, 1979

[54] SUBSTITUTED THIOPHENES

[75] Inventor: George G. I. Moore, Birchwood, Minn.

[73] Assignee: Riker Laboratories, Inc., Northridge, Calif.

[21] Appl. No.: 893,988

[22] Filed: Apr. 6, 1978

Related U.S. Application Data

[63] Continuation-in-part of Ser. No. 797,182, May 16, 1977, abandoned.

[51] Int. Cl.$^2$ ............... C07D 333/16; A61K 31/38
[52] U.S. Cl. ..................... 549/72; 424/275; 549/78
[58] Field of Search ............. 260/332.3 R, 332.3 C, 260/332.5

[56] References Cited

U.S. PATENT DOCUMENTS

| | | | |
|---|---|---|---|
| 3,711,554 | 1/1973 | Engelhardt et al. | 560/53 |
| 3,832,354 | 8/1974 | Gadient et al. | 260/332.3 R |
| 4,072,705 | 2/1978 | Mieville | 260/332.3 R |

OTHER PUBLICATIONS

Hucek, A. M., Phenolic Peresters, I. Radical and Induced Decomposition, J. Am. Chem. Soc. 95, (1973), pp. 4698-4705.

Hartough, Howard T., "Thiophene and its Derivatives", Interscience Publ., p. 29, (1952).

*Primary Examiner*—James O. Thomas, Jr.
*Assistant Examiner*—L. Hendriksen
*Attorney, Agent, or Firm*—Cruzan Alexander; Donald M. Sell; Donald C. Gipple

[57] ABSTRACT

3,5-Bis(t-butyl)-4-hydroxyphenyl- and 3,5-bis(t-butyl)-4-hydroxybenzoyl-substituted thiophenes have valuable pharmacological acitivity as antiinflammatory agents.

7 Claims, No Drawings

SUBSTITUTED THIOPHENES

This is a continuation-in-part of application Ser. No. 797,182, filed May 16, 1977, and now abandoned.

BACKGROUND OF THE INVENTION

This invention relates to 3,5-bis(t-butyl)-4-hydroxyphenyl- and 3,5-bis(t-butyl)-4-hydroxybenzoyl-substituted thiophenes (the thiophene ring being optionally also substituted by lower alkyl or halogen), to the use of such compounds as antiinflammatory agents and to novel intermediates useful for preparing final product compounds of the invention.

Thiophene compounds substituted by bis(t-butyl)-phenol groups have not been known previously. Insofar as applicant is aware, even thiophenes substituted by mono-t-butylphenol groups are not known. Compounds such as 4-(2'-thienyl)phenol, 4-(3'-thienyl)phenol, 3-(2'-thienyl)phenol, 3-(3'-thienyl)phenol and 2-(2'-thenoyl)-phenyl are known, however.

DETAILED DESCRIPTION OF THE INVENTION

This invention relates to 3,5-bis(t-butyl)-4-hydroxyphenyl- and 3,5-bis(t-butyl)-4-hydroxybenzoyl-substituted thiophenes which are active antiinflammatory agents. The invention also relates to a method for combatting inflammatory processes in mammalian animals by administering thereto an effective dose, less than the toxic amount, of such a compound of the invention and to antiinflammatory compositions comprising one or more such compounds together with a suitable pharmaceutical extending medium. The invention also relates to a novel class of chemical intermediates in the preparation of the final compounds of the invention.

Specifially the invention relates to compounds of the formula

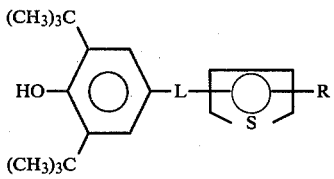

I wherein L is carbonyl or a carbon-carbon bond and R is hydrogen, methyl or halogen (fluorine, chlorine, iodine or bromine). Presently preferred, due to their ease of synthesis and high therapeutic ratio, are the compounds of formula I in which L is carbonyl, particularly those in which L is 2-carbonyl. Also, compounds of the invention wherein R is hydrogen or halogen are preferred, particularly those compounds wherein R is hydrogen or chlorine. In the compounds of the invention in which R is not hydrogen, it is preferred that L and R are not bonded to adjacent carbon atoms of the thiophene ring and that R is not iodine.

In addition to their use as effective antiinflammatory agents, the compounds of the invention are relatively active as stabilizers to prevent oxidation. Some also are analgesics, some are antipyretic agents, and some have mild immunosuppressant activity.

In order to determine and assess pharmacological activity, testing in animals is carried out using various assays known to those skilled in the art. Thus, the antiinflammatory activity of the compounds can be conveniently demonstrated using an assay designed to test the ability of these compounds to antagonize the local edema which is characteristic of the inflammatory response (the rat foot edema test). The compounds (I above) have also been found to inhibit the enzyme prostaglandin synthetase.

The prostaglandin synthetase inhibition assay is a broad screen for the detection of antiinflammatory activity and is carried out as follows. Buffer, substrate, cofactors, enzyme and drug samples are prepared:
  Buffer: 0.1 M Potassium phosphate, pH 7.4
  Substrate: 6 $\mu$M $^3$H-arachadonic acid (16 $\mu$Ci/$\mu$mole)
  Cofactors: Reduced glutathione and 1-epinephrine, 0.3 mg/$\mu$l each
  Enzyme: Microsomal extracts of bovine seminal vesicles are prepared from frozen tissue and diluted in 0.1 M tris-hydroxymethylaminomethane hydrochloride, pH 8.2, to 2-3 mg/ml protein
  Drugs: Dissolved in buffer or 50% methanol In the first step the microsomal extract (10 $\mu$l, 10-30 $\mu$g protein), cofactor solution (50 $\mu$l), drug or drug solvent (20 $\mu$l) and substrate (20 $\mu$l) are incubated at 37° C. for ten minutes. Blank assays contain all components, but are kept in an ice water bath.

In the next step $^3$H-arachadonic acid is separated from product prostaglandins (PGE$_2$+PGF$_{2\alpha}$) by column chromatography on silica gel (100-200 mesh). Solvent I (hexane:dioxane:acetic acid, 70/30/1) elutes the substrate followed by elution of prostaglandins with solvent II (ethyl acetate:methanol, 85/15). The column eluates are collected in scintillation vials, 10 ml. scintillation fluid is added and they are counted.

After subtraction of the blank, percent inhibition is calculated from the radioactivity recovered in the prostaglandin fraction:

$$\% \text{ Inhibition} = \frac{\text{Control} - \text{Drug}}{\text{Control}} \times 100$$

Drug Example: Indomethacin inhibits prostaglandin synthetase 84% at $5 \times 10^{-6}$ M; flufenamic acid inhibits 53% at $5 \times 10^{-6}$ M.

Reference: White, H. L. and Glossman, A. T.: A Simple Radiochemical Assay for Prostaglandin Synthetase. Prostaglandins 7(2):123-129 (1974).

The compounds of the invention are quite active when administered dermally. Such topical activity has been measured by means of the guinea pig erythema test and by a contact sensitivity test. Antiinflammatory activity may also be detected by other assays known to the art such as the cotton pellet granuloma test and the adjuvant arthritis test. The analgesic activity has been observed in standard test methods such as the phenylquinone writhing (mouse) and Randall-Selitto (rat) tests.

Leading references to the rat foot edema method are:
(1) Adamkiewicz et al, Canad, J. Biochem. Physio. 33:332, 1955;
(2) Selye, Brit. Med. J. 2:1129, 1949; and
(3) Winter, Proc. Exper. Biol. Med. 111:544, 1962.

The edema test is performed on adult female rats. One group of 10 rats serves as non-medicated controls, while another group of 10 rats receives the test compound at various times prior to the induction of the edema, usually 15 minutes, one hour and/or 18 hours. The test compound is administered orally as a suspension in 4 percent aqueous solution of acacia. Edema is induced by the plantar injection of 0.5 percent carrageenin (0.1 ml/foot) into the right hind foot. The left hind foot receives a like volume of 0.9 percent saline solution. One hour later, the volume of each hind foot is determined plethymographically. The edema is expressed as the increase in the volume of the edemogeninjected foot (volume of the "edemogen foot" less the volume of the "saline foot"). The percent inhibition is calculated by dividing the mean increase in the edema of the edemogen foot of the medicated group by the mean increase in the non-medicated group, multiplied by 100. An active dose is that giving a statistically significant inhibition of the induced edema, usually in the range of about 25–35 percent inhibition.

The compounds are preferably administered orally as antiinflammatory agents but other known methods of administration are contemplated as well, e.g. dermatomucosally (for example dermally, rectally and the like) and parenterally, for example by subcutaneous injection, intramuscular injection, intra-articular injection, intravenous injection and the like. Ocular administration is also included. Dosages ordinarily fall within the range of about 1 to 500 mg/kg of body weight of the mammal to be treated although oral dosages are not usually above 100 mg/kg. Suitable forms for oral administration include liquids (such as 4 percent acacia and polyethylene glycol solutions), tablets (which may contain anhydrous lactose, microcrystalline cellulose, modified starch, calcium stearate and talc, as well as other conventional compounding agents together with the active antiinflammatory agents), solid suspensions and capsules. Suitable carriers for topical application include creams, gels, tapes and the like. Liquid formulations, such as solutions or suspensions of the active ingredient in inert carriers, are contemplated for dosage by injection.

The presently preferred compounds of the invention with respect to antiinflammatory activity include 2,6-bis(t-butyl)-4-(2'-thenoyl)phenol, 2,6-bis(t-butyl)-4-(2'-thienyl)phenol, 2,6-bis(t-butyl)-4-(3'-thenoyl)phenol and 2,6-bis(t-butyl)-4-(5'-chloro-2'-thenoyl)phenol.

Presently preferred compounds of the invention with respect to dermal activity are 2,6-bis(t-butyl)-4-(2'-thenoyl)phenol and 2,6-bis(t-butyl)-4-(5'-chloro-2'-thenoyl)phenol.

The compounds of the invention wherein L is a carboncarbon bond are prepared readily by the reaction of 2,6-bis(t-butyl)benzoquinone with a Grignard reagent prepared from an appropriate halogenated thiophene. Halogenated thiophenes are well known to the art, as are procedures for their preparation. Among the known halogenated thiophenes are 2-iodothiophene, 2-bromothiophene, 2-chlorothiophene, 2-bromothiophene and the like.

Grignard reactions between the Grignard reagents of halogenated thiophenes and 2,6-bis(t-butyl) quinones provide the intermediate optionally substituted 2,6-bis(t-butyl)-4-(2'-thienyl)-2,5-cyclohexadien-1-ones having the formula:

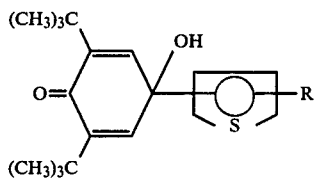

II wherein R is as previously defined (i.e. hydrogen, methyl or halogen). These compounds (II) are novel and fall within the scope of the present invention. They are reduced (using hydrogen gas and a catalyst such as palladium on charcoal or Raney nickel, a metal hydride reducing agent such as lithium aluminum hydride or hydrogen iodide) to form compounds of the invention of Formula I. As an alternative to using a Grignard reagent in the above reaction, known reactive equivalents such as lithium compounds are useful.

The compounds of the invention wherein L is a carbonyl group are prepared readily by several methods. The reaction of 3,5-bis(t-butyl)-4-hydroxybenzoyl chloride with optionally substituted thiophenes in the presence of Friedel-Crafts catalysts is useful for the synthesis of compounds wherein L is carbonyl bonded to the 2-position of thiophene and R is in the 5-position. Friedel-Crafts catalysts which are useful include aluminum chloride, titanium tetrachloride, zinc chloride and the like. The reactions are generally carried out by dissolving the benzoyl chloride in an inert solvent such as carbon disulfide, dichloroethane, dichloromethane and the like, optionally under an inert gas atmosphere such as nitrogen, adding the Friedel-Crafts catalyst at room temperature, and then adding the thiophene component dropwise, and allowing the reaction to progress to completion (as shown by completion of hydrogen chloride evolution). Heating or warming may sometimes be useful to promote the reaction.

Alternatively 2,6-bis(t-butyl)phenol can be reacted in the Friedel-Crafts reaction with an appropriate thiophenecarbonyl chloride. The procedure is essentially as above, using standard Friedel-Crafts techniques. A weaker catalyst such as titanium tetrachloride will be preferred if the reaction rate is too rapid with aluminum chloride. Another alternative is direct introduction of one or two tertiary butyl groups into the 4'-thienylphenylphenol or 4'-thenoylphenol nucleus by a Friedel-Crafts reaction.

Using the methods described hereinabove the preparation of compounds of the invention is illustrated using the following examples. The purpose of the examples is to enable those skilled in the art to practice the invention, and they are not intended to in any way limit the scope of the invention.

EXAMPLE 1

To a solution of 26.9 g. (0.10 mole) of 3,5-bis(t-butyl)-4-hydroxybenzoyl chloride in 300 ml. of carbon disulfide is added 13.5 g of aluminum chloride. After stirring 15 minutes and warming slightly 17 g. (0.104 mole) of 2-bromothiophene is added. The reaction mixture gradually turns from a green color to a maroon color. It is then poured into 10% hydrochloric acid, and extracted with dichloromethane. The extracts are dried, then the solvent is evaporated to provide an oil which readily crystallizes. Recrystallization from hexane with treatment with decolorizing charcoal provides 2,6-bis(t-butyl)-4-(5'-bromo-2'-thenoyl)phenol, m.p. 126°–127.5° C.

| Analysis: | %C | %H |
| --- | --- | --- |
| Calculated for $C_{19}H_{23}BrO_2S$: | 57.7; | 5.9 |
| Found: | 57.6; | 5.9. |

EXAMPLE 2

Using the method of Example 1 and adding 0.1 mole of 2-methylthiophene in carbon disulfide one obtains 2,6-bis(t-butyl)-4-(5'-methyl-2'-thenoyl)phenol, m.p. 126°–127.5° C. after two recrystallizations from benzene-hexane mixtures.

| Analysis: | %C | %H |
|---|---|---|
| Calculated for $C_{20}H_{26}O_2S$: | 72.7; | 7.9 |
| Found: | 73.2; | 8.0. |

EXAMPLE 3

Using the method described in Example 2, 0.1 mole of 2-chlorothiophene is reacted to provide 2,6-bis(t-butyl)-4-(5'-chloro-2'-thenoyl)phenol, m.p. 114.5°–115.5° C.

| Analysis: | %C | %H |
|---|---|---|
| Calculated for $C_{19}H_{23}ClO_2S$: | 65.0; | 6.6 |
| Found: | 65.1; | 6.7. |

EXAMPLE 4

Using the method of Example 1 with thiophene as the reactant one obtains 2,6-bis(t-butyl)-4-(2'-thenoyl)phenol, m.p. 129°–130.5° C.

| Analysis: | %C | %H |
|---|---|---|
| Calculated for $C_{19}H_{24}O_2$: | 72.1; | 7.6 |
| Found: | 72.3; | 7.7. |

EXAMPLE 5

A Grignard reagent of 0.0181 mole of 2-bromothiophene is prepared by reaction with 0.45 g. of magnesium in diethyl ether. This reagent is added to a solution of 4.0 g. (0.018 mole) of 2,6-bis(t-butyl)benzoquinone in 75 ml. of diethyl ether. The mixture is heated to its reflux temperature and maintained at reflux for about 5 hours. The product obtained is 2,6-bis(t-butyl)-4-hydroxy-4-(2'-thienyl)-2,5-cyclohexadien-1-one. It is used in the next step as the mixture obtained. To this mixture is added cautiously a slight excess of lithium aluminum hydride. After stirring for about sixteen hours at room temperature water is cautiously added, then 10 percent hydrochloric acid. The mixture is extracted with dichloromethane, the extracts are dried, then evaporated to provide an oil. The oil is extracted with petroleum ether, then the extracts are cooled at -20° for about sixteen hours. The product is separated by filtration, then sublimed at 80°–82° C./0.1 mm. Hg. Recrystallization from hexane provides 2,6-bis(t-butyl)-4-(2'-thienyl)phenol, m.p. 93°–94° C.

| Analysis: | %C | %H |
|---|---|---|
| Calculated for $C_{18}H_{24}OS$: | 74.9; | 8.4 |
| Found: | 75.2; | 8.6. |

EXAMPLE 6

Thiophene-3-carboxylic acid is converted to the acid chloride by reaction with thionyl chloride. Thiophene-3-carbonyl chloride is isolated by distillation at 80°–85° C./0.25 mm.

A solution of 14.66 g. (0.10 mole) of thiophene-3-carbonyl chloride in 100 mg. of dichloroethane is added to 20.87 g. (0.1 mole) of titanium tetrachloride. To this solution is added 0.10 mole of 2,6-bis(t-butyl)phenol in a minimum amount of dichloroethane. The mixture is stirred for about sixteen hours, then poured into 500 ml. of 10% hydrochloric acid. The organic layer is separated, washed with water and dried. The solvent is evaporated to provide an oil which is mixed with hexane and cooled. The product is separated and recrystallized from hexane to provide, 2,6-bis(t-butyl)-4-(3'-thenoyl)phenol, m.p. 101°–102° C., then 127°–218° C. in an apparent change of crystal structure.

| Analysis: | %C | %H |
|---|---|---|
| Calculated for $C_{19}H_{24}O_2S$: | 72.1; | 7.7 |
| Found: | 72.0; | 7.8. |

EXAMPLE 7

Using the method of Example 1, 3,5-bis(t-butyl)-4-hydroxybenzoyl chloride is reacted with 2-fluorothiophene to provide 2,6-bis(t-butyl)-4-(5'-fluoro-2'-thenoyl)phenol.

EXAMPLE 8

Using the method of Example 6, 5-chlorothiophene-3-carbonyl chloride is reacted with 2,6-bis(t-butyl)phenol to provide 2,6-bis(t-butyl)-4-(5'-chloro-3'-thenoyl)phenol.

EXAMPLE 9

Using the method of Example 6, 5-fluorothiophene-3-carbonyl chloride is reacted with 2,6-bis(t-butyl)phenol to provide 2,6-bis(t-butyl)-4-(5'-fluoro-3'-thenoyl)phenol.

EXAMPLE 10

Using the method of Example 5, the Grignard reagent of 4-bromo-2-fluorothiophene is reacted with 2,6-bis(t-butyl)benzoquinone to provide 2,6-bis(t-butyl)-4-(5'-fluoro-3'-thienyl)phenol.

EXAMPLE 11

To a solution of 0.2 mole of 3,5-bis(t-butyl)-4-hydroxybenzoyl chloride in dichloroethane is added 42 g. (0.20 mole) of 2-iodothiophene.

This solution is added dropwise to 37.9 g. (0.20 mole) of titanium tetrachloride in 200 ml. of dichloroethane at about 5° C. over about 30 minutes. The solution is allowed to warm to 20° C. and is stirred for 48 hours. It is then poured into ten percent hydrochloric acid and the organic layer is separated, washed with water, dried and evaporated to dryness. The residue obtained is washed with hexane, then recrystallized from methanol. The product is again extracted and washed with a hot (90/10) hexane/toluene mixture. The pale yellow solid is again recrystallized from methanol to provide 2,6-bis(t-butyl)-4-(5'-iodo-2'-thenoyl)phenol, m.p. 145.5°–147° C.

| Analysis: | %C | %H |
|---|---|---|
| Calculated for $C_{19}H_{23}IO_2S$: | 51.8; | 5.3 |

| Analysis: | %C | %H |
|---|---|---|
| Found: | 51.7; | 5.4. |

EXAMPLE 12

To a solution of 3.8 g. (0.02 mole) of titanium tetrachloride in 50 ml. of dichloroethane under nitrogen is added a dichloroethane solution of 3.21 g. (0.02 mole) of 4-methyl-thiophene-2-carbonyl chloride. The solution is then cooled with an ice bath, and 4.12 g. (0.02 mole) of 3,5-di(t-butyl)phenol in dichloroethane is added dropwise over 30 minutes. The mixture is stirred for about 20 hours, then filtered through silica gel, eluting with a mixture of hexane/chloroform (20/80). Recrystallization from hexane provides white solid 2,6-bis(t-butyl)-4-(4'-methyl-2'-thenoyl)phenol, m.p. 111.5°–113° C.

| Analysis: | %C | %H |
|---|---|---|
| Calculated for C$_{20}$H$_{26}$O$_2$S: | 72.7; | 7.9 |
| Found: | 73.3; | 7.9. |

EXAMPLE 13

Using the method of Example 1 and adding 0.1 mole of 3-methylthiophene in carbon disulfide, 2,6-bis(t-butyl)-4-(3'-methyl-2'-thenoyl)phenol, m.p. 105.5°–107.5° C.) is obtained.

| Analysis: | %C | %H |
|---|---|---|
| Calculated for C$_{20}$H$_{26}$O$_2$S: | 72.7; | 7.9 |
| Found: | 72.7; | 8.0. |

EXAMPLE 14

Using the method of Example 1 and adding 0.1 mole of 3-bromothiophene in carbon disulfide, 2,6-bis(t-butyl)-4-(3'-bromo-2'-thenoyl)phenol, m.p. 116°–118° C., is obtained.

| Analysis: | %C | %H |
|---|---|---|
| Calculated for C$_{19}$H$_{23}$BrO$_2$S: | 57.7; | 5.8 |
| Found: | 58.2; | 6.1. |

What is claimed is:
1. A compound of the formula

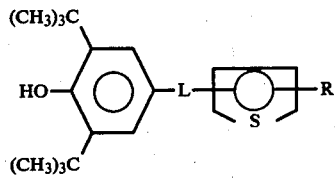

wherein L is carbonyl or a carbon-carbon bond and R is hydrogen, methyl or halogen.

2. A compound according to claim 1 wherein R is hydrogen.

3. A compound according to claim 1 wherein L is carbonyl.

4. The compound 2,6-di(t-butyl)-4-(2'-thenoyl)phenol according to claim 1.

5. The compound 2,6-di(t-butyl)-4-(3'-thenoyl)phenol according to claim 1.

6. The compound 4-(5'-chloro-2'-thenoyl)-2,6-di(t-butyl)phenol according to claim 1.

7. The compound 2,6-di(t-butyl)-4-(2'-thienyl)phenol according to claim 1.